US012440390B2

(12) United States Patent
Lipshaw et al.

(10) Patent No.: US 12,440,390 B2
(45) Date of Patent: *Oct. 14, 2025

(54) COMPRESSION GARMENT

(71) Applicant: MEDI USA, L.P., Whitsett, NC (US)

(72) Inventors: Moses Lipshaw, Whitsett, NC (US); Thomas Richardson, Whitsett, NC (US); Dean Bender, Whitsett, NC (US); Karen Lynch, Whitsett, NC (US); Kevin Larmer, Whitsett, NC (US)

(73) Assignee: Medi USA, L.P., Whitsett, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/742,130

(22) Filed: Jun. 13, 2024

(65) Prior Publication Data

US 2024/0335332 A1 Oct. 10, 2024

Related U.S. Application Data

(63) Continuation of application No. 17/683,333, filed on Feb. 28, 2022, now Pat. No. 12,036,097, which is a continuation of application No. 16/312,253, filed as application No. PCT/US2017/040293 on Jun. 30, 2017, now Pat. No. 11,517,482.

(60) Provisional application No. 62/356,992, filed on Jun. 30, 2016.

(51) Int. Cl.
*A61F 13/14* (2006.01)
*A61F 5/02* (2006.01)
*A61F 5/03* (2006.01)
*A61F 5/37* (2006.01)

(52) U.S. Cl.
CPC .............. *A61F 13/143* (2013.01); *A61F 5/02* (2013.01); *A61F 5/37* (2013.01); *A61F 13/14* (2013.01); *A61F 5/03* (2013.01)

(58) Field of Classification Search
CPC .......... A61F 13/14; A61F 13/143; A61F 5/02; A61F 5/03; A61F 5/37
See application file for complete search history.

(56) References Cited

U.S. PATENT DOCUMENTS 8,801,645 B2 * 8/2014 Lipshaw ................ A61H 99/00 450/101
2013/0319128 A1 * 12/2013 Richardson ............ A61B 5/103 73/818

FOREIGN PATENT DOCUMENTS

DE 202012002221 U1 * 8/2013 ............ A61F 13/14

* cited by examiner

*Primary Examiner* — Keri J Nelson
(74) *Attorney, Agent, or Firm* — Rimon PC

(57) ABSTRACT

A compression garment is disclosed. The garment can include a body dimensioned to wrap at least partially around a length of a torso of a user. A plurality of tension bands can be positioned along the body. The garment can include at least one shoulder strap, wherein the shoulder strap is operable to wrap over the shoulder of the user to hold the garment in position.

15 Claims, 11 Drawing Sheets

COMPRESSION GARMENT

CROSS REFERENCE TO RELATED APPLICATIONS

This present application is a continuation of U.S. application Ser. No. 17/683,333 filed on Feb. 28, 2022, which is a continuation of U.S. application Ser. No. 16/312,253, filed Dec. 20, 2018, which is a United States national stage entry of International Patent Application No. PCT/US2017/040293 filed Jun. 30, 2017, which claims priority to U.S. Provisional Patent Application Ser. No. 62/356,992, filed Jun. 30, 2016. The contents of each of these applications are incorporated herein by reference herein in their entirety.

FIELD

Compression garments to support and assist with pain management for post open heart surgery support, post mastectomy support or compressive therapy for truncal lymphedema.

BACKGROUND

Lymphedema is swelling that occurs when excessive protein-rich lymph fluid accumulates in the interstitial tissue. This lymph fluid may contain plasma proteins, extravascular blood cells, excess water, and parenchymal products. Lymphedema is one of the most poorly understood, relatively underestimated, and least researched complications of common diseases like cancer, and thus the prevalence of lymphedema within the general population is largely unknown. Nevertheless, for those who are diagnosed with lymphedema, the standard of care consists of meticulous skin care, manual lymphatic drainage, exercise therapy, inelastic compression bandaging and, eventually, compression garments. In regard to truncal lymphedema in particular, this condition relates to those who experience excessive fullness and/or pain in the breast, chest, lateral trunk, armpit or back are living with post-treatment discomfort.

The frequency and duration of care is dependent on individual subject's therapeutic need and may range from 2 to 3 visits per week for 6 or more weeks depending on the severity of lymphedema and any other associated impairment.

The use of compression bandaging, although proven effective in reducing edema, has its drawbacks. The application of inelastic compression bandages is time consuming and requires a skilled clinician. Furthermore, because subjects are not able to effectively bandage themselves, this treatment strategy does not promote self-care, does not provide sustained therapeutic levels of compression, and requires the subject to frequently return for follow up visits. Lastly, wearing bandages negatively impacts the subject's quality of life with regard to comfort and hygiene which can reduce compliance.

Many bandage alternative wrap type garments exist on the market. These garments are primarily used after the intensive phase treatment of lymphedema to maintain the patient's limb size. Most of the wrap garments lack the ability to adapt to changes in limb size and are cost prohibitive to be used as a short term bandage replacement in the intensive phase. For those garments that are available the sizing adjustments can be complex and time consuming for practical use. The embodiments of the present disclosure address these and other related needs in the art.

SUMMARY

In some embodiments, a compression garment is disclosed. The garment can include a body dimensioned to wrap at least partially around a length of a torso of a user. A plurality of tension bands or other closure systems can be positioned along the body. The garment can include at least one shoulder strap, wherein the shoulder strap is operable to wrap over the shoulder of the user to hold the garment in position.

In some embodiments, the at least one shoulder strap extends away from an upper edge of the body. The at least one strap can include one or more compression portions. The one or more compression portions can be inelastic and/or upraised portion(s) selectively positioned and operable to apply pressure to an area of the user. One or more compression portions can also be detachably connected to the at least one strap. The at least one shoulder strap could also extend from a lower edge of the body (e.g. in those embodiments when the compression garment is configured for genital compression support and/or as a garter to hold one or more other garments in place.).

In some embodiments, a distal end of the shoulder strap is releasably attached onto the body. A proximal end of the shoulder strap can be on or adjacent the upper edge of the body, the proximal end being fixedly attached to the body.

In some embodiments, the at least one shoulder strap extends substantially orthogonal to the tension bands. The at least one shoulder strap can also be extendible about a shoulder of the user (e.g. in the manner and shape of t-shirt).

In some embodiments, the body can include indicia for shortening a length of the garment. The body can also include one or more pockets.

In some embodiments, the body can include a top edge, a bottom edge and a pair of opposite side edges, wherein the body can be trimmable between the edges permitting the body to correspond to any shape of torso.

In some embodiments, the body can include indicia for trimming along a region of the body about or in communication with the axilla. The body can also include indicia for indicating the axilla. The body, one or more of the tension bands, and/or the at least one shoulder strap can include indicia indicating a dimension of the user. The dimension can relate to one or more of the shoulder, circumference of the upper chest, the lower chest, waist, torso, and/or the pectorals.

In some embodiments, the tension bands can be of a stiffer material and the body can be more elastic or formed from otherwise stretchable, flexible material. The tension bands can be of a different elasticity and stiffness than the body material. The elastic and/or flexible material can be capable of folding and conforming to contours of the torso thereby rendering the garment less constricting. The stiffer material can bridge folds and contours of the body to provide a more comfortable and shaping fit. The body can include an inner surface and an outer surface, the outer surface being stiffer or less flexible or less elastic than the inner surface. The body can include an inner surface and an outer surface, the outer surface being a different stiffness than the inner surface In some embodiments, the tension bands can be stiffer and less elastic, and/or less flexible than the body. One or more of the tension bands can also be trimmable to adjust or conform to the torso, including its size and shape, of the user.

In some embodiments, one or more of the tension bands can be trimmable and include indicia for trimming. The at least one shoulder strap can be trimmable and/or include indicia for trimming. The body further can include one or more fasteners releasably attached thereon. The one or more fasteners can be positioned along a contoured edge of the body. The at least one shoulder strap can include one or more fasteners releasably attached thereon.

In some embodiments, the garment can include one or more additional shoulder straps. Each the tension bands can be operable to secure opposing edges of the body around the torso.

In other embodiments, a compression garment in accordance with this disclosure that can include a pair of shoulder straps. Each shoulder strap can be disposed on opposite sides of a collar portion of the body, each shoulder strap can be operable to wrap over the shoulder of the user to hold the garment in position.

In some embodiments, one or both shoulder straps extend away from an upper edge of the body or a lower edge of the body. One or both shoulder straps can include one or more of the previously described compression portions. One or more compression portions can be detachably connected to one or both shoulder straps. A distal end of one or both shoulder straps can be releasably attached onto the body.

In some embodiments, a proximal end of one or both shoulder straps can be on or adjacent the upper or lower edge of the body, the proximal end being fixedly attached to the body.

In some embodiments, one or both shoulder straps extend substantially orthogonal to the tension bands. One or both shoulder straps can be extendible about a shoulder of the user as a t-shirt.

In some embodiments, the body, one or more of the tension bands, and/or one or both shoulder straps further comprises indicia indicating a dimension of the user. The dimension can relate to one or more of the shoulder, circumference of the upper chest, the lower chest, the torso, and/or the pectorals. In some embodiments, one or more additional shoulder straps can also be included with the garment.

In some embodiments, each of the tension bands is operable to secure opposing edges of the body around the torso.

In other embodiments, a compression garment in accordance with this disclosure that can include a body dimensioned to wrap at least partially around a length of a torso of a user. A spine portion can be releasably positionable onto the body at a plurality of positions. A plurality of tension bands can be extended from the spine portion. At least one shoulder strap can be extended from the body or the spine portion. The at least one shoulder strap can be operable to wrap over the shoulder of the user between two positions of the body and/or spine portion to hold the garment in position.

In some embodiments, the spine portion can be independently angleable on the body at a plurality of orientations. The spine portion can be positionable along a curved edge of the body. In some embodiments, the body can be elastic and the spine portion can be limited stretch, substantially inelastic, or inelastic. However, the garment is not so limited and instead the spine portion can be elastic and the body can be limited stretch, substantially inelastic, or inelastic.

In some embodiments, the tension bands can be substantially elastic and the body and spine portions can be inelastic or include one or more inelastic portions. The at least one shoulder strap can be extended away from an upper or lower edge of the body. The at least one shoulder strap can also include one or more compression portions, as described herein. A distal end of the at least one shoulder strap can be releasably attached onto the body between one of a plurality of different positions and/or orientations. A proximal end of the at least one shoulder strap can be on or adjacent the upper or lower edge of the body while the proximal end can be fixedly attached to the body (e.g., sewn, adhered, etc.).

In some embodiments, the at least one shoulder strap can extend substantially orthogonal to the tension bands. In some embodiments, the at least one shoulder strap can be extendible about a shoulder of the user as a t-shirt. In some embodiments, the body can include indicia for shortening a length of the garment.

In some embodiments, the body can include one or more pockets. The pockets may be releasably positionable to the body of the garment. In some embodiments, the pockets can be positioned externally on the garment. In other embodiments, the pockets can be positioned internal to the garment. For example, one or more internally positioned pockets can be used with foam padding or other compression materials or compression portions disposed inside the garment against the limb of the user to hold the pockets in place. In some embodiments, the body can include one or more holes, slits, or indicia to cut or otherwise provide access points to the interior of the garment and user's body. These access points can have multiple purposes including pathways for patient leads and monitoring equipment.

In some embodiments, the body can include indicia for trimming along a region of the body about or in communication with the axilla. The indicia can be configured for indicating the axilla.

In some embodiments, the body, one or more of the tension bands, and/or the at least one shoulder strap can include indicia indicating a dimension of the user. The dimension can relate to one or more of the shoulder, circumference of the upper chest, the lower chest, the torso, and/or the pectorals.

In some embodiments, the tension bands can be of a stiffer material and the body can be of an elastic material. The elastic material can be capable of folding and conforming to contours of the body part thereby rendering the garment less constricting.

In some embodiments, one or more of the tension bands are trimmable and include indicia for trimming. The at least one shoulder strap can also be trimmable and/or include indicia for trimming.

In some embodiments, the body, tension bands, and/or at least one shoulder strap can include one or more fasteners releasably attached thereon. In some embodiments, one or more additional shoulder straps can also be included with the garment. In some embodiments, each of the tension bands can be operable to secure opposing edges of the body around the torso.

In other embodiments, a compression garment in accordance with this disclosure that can include a plurality of spine portions. A plurality of tension bands can be positioned along the spine portion. At least one edge or region of each spine portion can be trimmable such that each spine portion can be releasably positionable onto the body at a plurality of positions. At least one adjustable shoulder strap can be extended from the body or the spine portion. The at least one shoulder strap can be operable to wrap over the shoulder of the user between two positions of the garment to hold the garment in position.

In some embodiments, the plurality of spine portions consists of two spine portions, each portion being removably positioned on opposing sides, side edges, or regions of the body. Each spine portion in this embodiment can be disposed on opposite sides or regions of the body. In some embodiments, the body and/or the spine portions are trimmable from top to bottom edges permitting the body and/or the spine portions to correspond to a size and a shape of the torso.

In some embodiments, each spine portion is independently angleable on the body at a plurality of orientations. Each spine portion can be positionable along a curved edge of the body. In some embodiments, the body is elastic and the spine portions are non-elastic. In other embodiments, the spine portions are elastic and the body is non-elastic. In some embodiments, the tension bands can be substantially elastic and the body and spine portions can be non-elastic or include one or more non-elastic portions.

In some embodiments, the at least one shoulder strap can extend away from an upper or lower edge of the body. The at least one shoulder strap can include one or more compression portions. In some embodiments, a distal end of the at least one shoulder strap is releasably attached onto the body. In some embodiments, a proximal end of the at least one shoulder strap can be on or adjacent the upper or lower edge of the body. The proximal end can be fixedly attached to the body (e.g. adhered thereto, sewn, etc.).

In some embodiment, the garment can be operable to be an anchor point for one or more compression garments (e.g., sleeves for arms or legs, leggings, head/neck, or wraps for etc. For example, one or more other compression garments can be releasably attached onto the garment of this disclosure to make attachment (.)

In some embodiments, a compression and/or tension level measuring system is provided with the garment for indicating an actual compression level delivered to the torso by the garment. The system can be operable to measure indicia of the garment when the garment is donned by the torso. The system can include a card having a scale for measuring a separation of at least one indicia to determine an actual compression level to the torso associated with the separation. At least one end of the tension band is releasably attachable to a plurality of locations and orientations so that the tension band is adjustable between a plurality of compression levels according to the actual compression level measured by the system. In some embodiments, the system is disposed on the body, shoulder strap, spine portion(s), and/or tension bands. The system can include a stretchable base layer and an upper layer attached at two spaced-apart locations on top of the stretchable base layer. A visual indicator of the actual compression level can be positioned with the upper or base layers and is observable when the upper layer is pulled taut.

In other embodiments, a method of fitting a compression garment to a torso is disclosed. The method can include selectively positioning a plurality of tension bands on a body of the garment; selectively positioning a plurality of shoulder straps on the body of the garment; wrapping the body around part of the torso; wrapping each of the tension bands around part of the torso to apply a therapeutic compression to the torso; and extending each of the shoulder straps between two locations on the garment around part of the torso about the shoulder.

In some embodiments, the method can also include extending the shoulder straps substantially normal to tension bands. In some embodiments, the method can also include trimming the body to a preferred size prior to attaching the tension bands, by: measuring a dimension of the torso at one or more locations, and trimming the body such that top and bottom edges of the body correspond to the torso at each of the one or more locations.

In some embodiments, wrapping each of the tension bands around part of the torso can include pulling together opposite side edges of the body, and wrapping the tension bands across the opposite side edges of the body.

In some embodiments, the body includes a central region and two detachable spine portions, the tension bands extending away from each spine portion. In this regard, the method can include selectively positioning each spine portion onto the central region on opposing side edges. Each side edge of the spine portion can be contoured.

In some embodiments, the method can also include selectively positioning the garment about the user by positioning the shoulder straps with the shoulders of the user thereby preventing the garment from sliding down the torso. In some embodiments, the method can also include juxtaposing the tension bands between one another when being wrapped around the part of the torso. In some embodiments, the method can also include positioning indicia on the body and/or tension bands and/or shoulder strips, the indicia corresponding to a dimension of the user; and trimming the body and/or tension bands and/or shoulder straps according to the indicia.

To the accomplishment of the foregoing and related ends, certain illustrative aspects are described herein in connection with the following description and the annexed drawings. These aspects are indicative, however, of but a few of the various ways in which the principles of the claimed subject matter may be employed and the claimed subject matter is intended to include all such aspects and their equivalents. Other advantages and novel features may become apparent from the following detailed description when considered in conjunction with the drawings.

DETAILED DESCRIPTION

Figure 1:
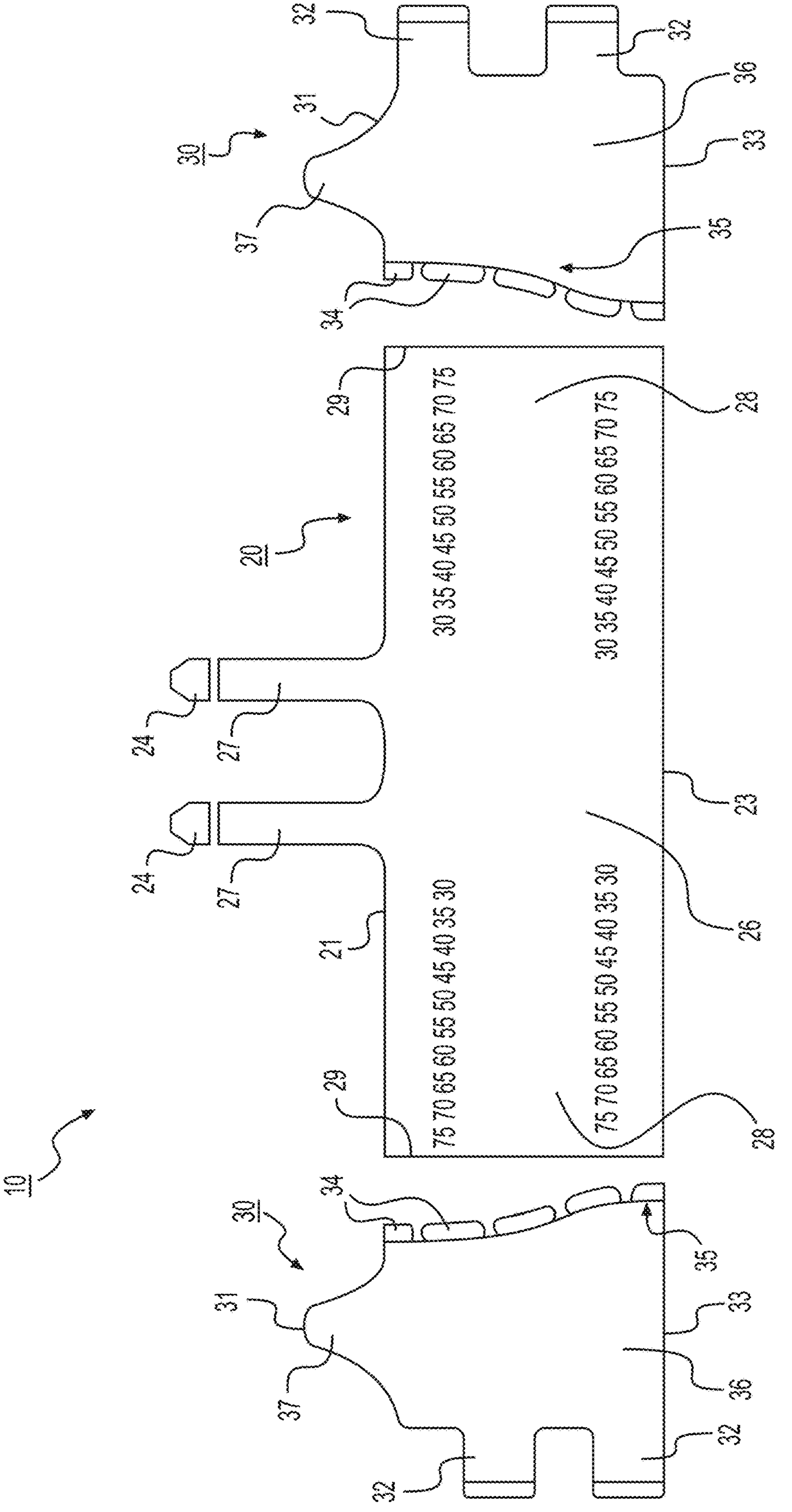
FIG. 1 depicts a top plan view of one exemplary embodiment of a compression garment of this disclosure in an unassembled state.

Unless defined otherwise, all terms of art, notations and other scientific terms or terminology used herein have the same meaning as is commonly understood by one of ordinary skill in the art to which this disclosure belongs. In some cases, terms with commonly understood meanings are defined herein for clarity and/or for ready reference, and the inclusion of such definitions herein should not necessarily be construed to represent a substantial difference over what is generally understood in the art. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more."

As used herein, the term "subject" is not limited to a specific species. For example, the term "subject" may refer to a patient, and frequently a human patient. However, this term is not limited to humans and thus encompasses a variety of mammalian species.

As used herein, the term "elastic" as it pertains to compression garments can relate to garments and/or materials and/or portions of garments that can be stockings, wraps, or any portion thereof, both circular and flat knit, which can incorporate elastic fibers such as spandex or latex. It is this elastic fiber that enables the garment to provide compression and also to stretch in order to apply the garment to the limb. Because of the elastic nature of the garment in this respect, a consistent or static compression to the limb can be applied; when an individual changes position, such as moving from supine to standing, the limb circumference changes. This elastic nature stretches to accommodate the change in circumference and maintains a fairly consistent compression level regardless of position or movement. This is particularly beneficial when a patient experiences a reduction in limb size due to the removal of excess edema in the treated limb. However it also requires that the compression garment be removed when in a supine position because a consistent high compression level may result in pain in the limbs due to the decreased venous pressure.

As used herein, the term "non-elastic" or "inelastic" can be the opposite or substantially opposite of elastic materials and/or elastic compression. Garments, or constituent materials that are non-elastic, may not stretch, or may have limited stretch when a limb circumference changes (e.g. as the result of body movement). A non-limiting example of non-elastic material can be Velcro 3610 though other material or combination of materials can be included with less or more stretch and still qualify as non-elastic as that term is used herein. Other non-limiting examples of limited stretch material can be breathoprene, neoprene, and similar laminates and/or materials that are able to be utilized in inelastic compression designs.

As used herein, the term "substantially" or "substantial" is a meaningful modifier implying "approximate" rather than "perfect." For example, the term "substantially normal" can be used as it will be appreciated that a reference edge or reference line of a particular portion of the garment may not be perfectly "normal."

Compression therapy is considered the mainstay of treatment for lymphedema which relies on the application of external force in order to increase the internal pressure of the affected limb. Almost any portion of the body can suffer from swelling. Additionally, following open heart surgery, compressive support is critical for managing pain and preventing strain on the surgery site. There are several approaches to resolve these and other problems of the art.

A first approach has included a compression vest that is capable of opening and closing as needed (e.g. via a zipper). This is the most common method of support and the approach relies on the elasticity of the vest material to provide the requisite compression. Some vests have included pockets and relatively small holes where devices such as cardiac monitors and lead wires can be placed.

However, vests that utilize elastic materials and such zipper-like closure mechanisms can be difficult to don and offer no means of adjustment. Additionally, such vests provide limited compression. Unfortunately, for the garments to provide adequate support, the user needs to pull the opposing sides of the vest together before being able to secure the zipper which requires a certain degree of strength and can be difficult for many users with limited strength (e.g. elderly patients and/or children). These problems are exacerbated by the fact that in order to combat the difficulty posed by the zipper closure mechanism, the materials used in these vests are often very elastic so that the user can more easily stretch the garment to close.

Consequently, the compression of such elastic vests is limited and offer minimal support. Zipper compression vests made from more inelastic materials offer more substantial compression but are more difficult to apply. To address this limited compression and the difficulty of donning inelastic compression vests, vest manufacturers have provided a pillow that the user can squeeze against their chest when additional support is needed, such as while sneezing or coughing. Similarly, air bladders can be included in order to apply the compression. In this regard, although these elastic vests may be easy to don, they are also prohibitively expensive due to the increased elements and structure and can only be used while stationary.

A second approach has included vests that fail to encompass the entire torso and instead focus more on just supporting the surgical sight. The support provided by the vest in this approach is achieved through the use of elastic materials. The most significant support, however, is provided by the user holding onto handles on both sides of the wound and pulling them together. These vests also address inadequate support by enabling the user to proactively increase compression levels in times of need. The vest includes handles that can be held together in situations where additional support is needed, such as while sneezing or coughing. This can be effective but does require the user to identify when they will need added compression ahead of time and also requires that the user's torso is empty and available to help.

Similar to open heart surgery, mastectomy operations also require post-surgical support to assist with pain management and healing. In this regard, a third approach for vests directed towards post mastectomy support has included bra-like products that function virtually the same way as a standard bra. However, these bra-like products offer more robust closure systems ranging from clips to strips of hook and loop. These bra-like products are both limited in the amount of compression they can apply and can also be difficult to close. Moreover, sizing is very specific and comfort is often a concern, if not lacking.

For truncal edema therefore, the most common treatment are either a full vest, or bra-like product similar to the aforementioned approaches. Vests typically rely on the elasticity of the material or can utilize pillows or air bladders that provide therapeutic compression once inflated.

As can be seen, FIG. 1 depicts a top plan view of one exemplary embodiment of a compression garment 10 of this disclosure in an unassembled state. The garment 10 can include a body 20 that is dimensioned to wrap at least partially around a length of a torso of a user. A plurality of tension bands 32 can be positioned along the body 20. In the embodiment depicted, bands 32 are shown extending from a separate spine portion 30 on each side of body 20. However, the garment 10 is not so limited and instead each of those bands 32 could be integrally formed or otherwise extended from body 20 without the need for a separate spine portion 30. There could be only one spine portion 20 or more than two spine portions 20, as depicted.

Figure 3:
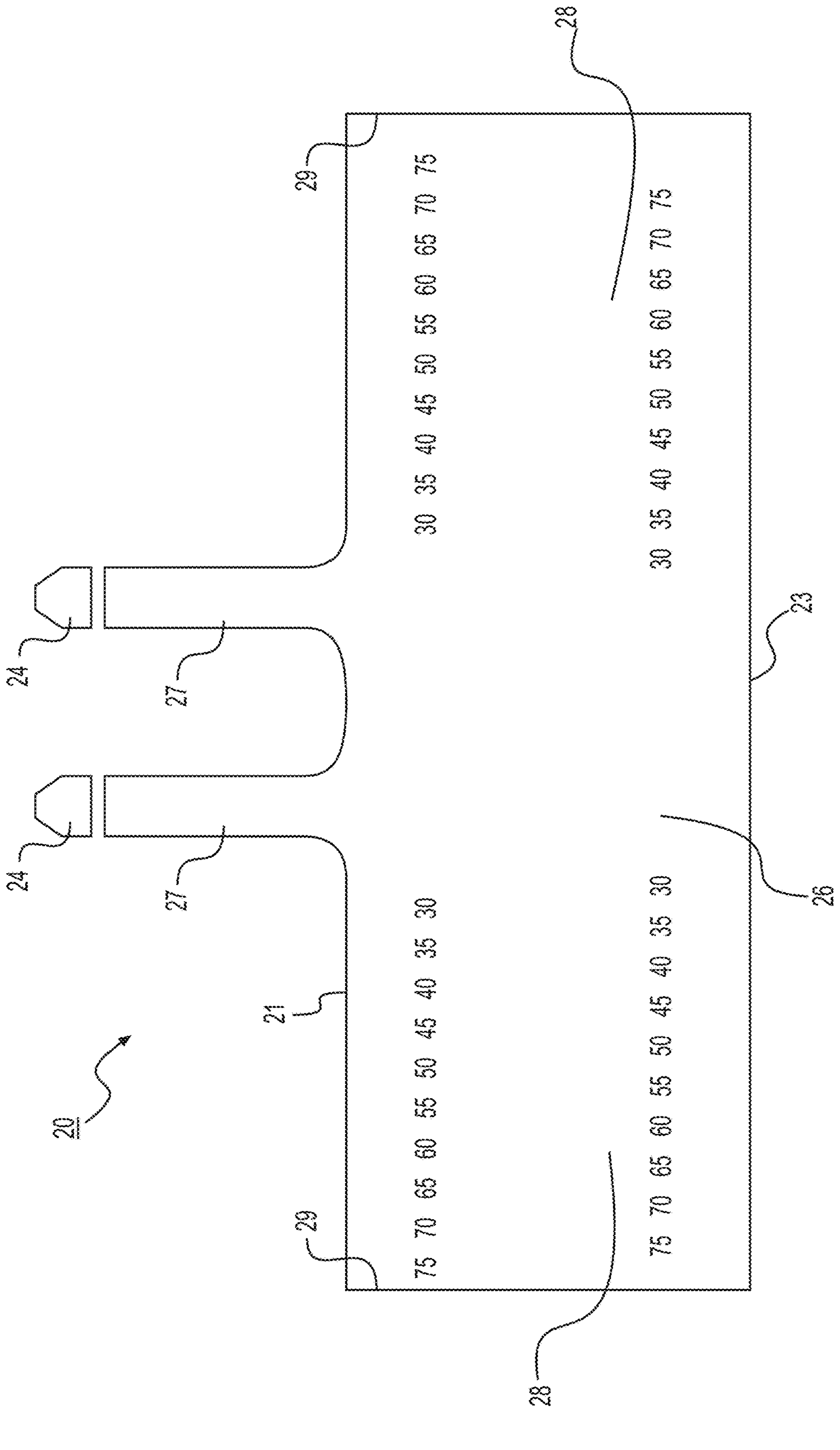
FIG. 3 depicts a close-up top plan view of an example body of a compression garment of this disclosure.

As more clearly shown in FIG. 3, body 20 can include a central region 26 and one or more lateral regions 28. As shown, each of these regions 26, 28 can be formed from the same article or can be formed from separate articles or can be otherwise delineated with seams or the like. Regions 28 can include lateral side edges 29 that can be contoured with one or more curved edges, a substantially straight edge, or some combination thereof. As shown, the body 20 can include indicia for shortening a dimension (e.g. the length) of the garment 10, whereby the indicia as shown can be the smaller numbers imprinted on body 20 that can correspond to dimension of the user. As can be seen, indicia of body 20 may be one or more alphanumeric characters (e.g. the relatively small numbers listed between 30-75) positioned on body 20 by being printed, painted, glued, heat transferred, sewn onto or otherwise attached thereon. The indicia can be positioned in one or more regions of body 20 as well. For example, as shown, there may be indicia on or adjacent the upper edge 21, on or adjacent the lower edge 23, in one or more of the lateral regions 28, the central region 26, or anywhere on the body to be able to accurately and easily trim the body 20 to conform to the body part of the user. In some embodiments, body 20 can be trimmable between the edges 21, 23, 29 permitting the body 20 to correspond to any shape of the torso. Indicia of body 20 could also be dots, geometric shapes, symbols, patterns, tick marks, text, standard size designators (e.g., S, M, L, XL, etc.) or the like spaced at intervals therealong The garment 10 can also include at least one shoulder strap 27. As shown, there can be only two straps 27, one configured to be positioned on each side of the user's shoulder. However, only one strap 27 could be used or more than two straps 27 as needed or required. As shown, strap 27 can be formed by one or more curved edges disposed on the upper edge 21 of body 20. However, strap 27 is not so limited and instead only one curved edge could be present or no curved edges on edge 21 could be present. Additionally, strap 27 could be detachably connected at its proximal end on the body 20 to accommodate different sized and shaped torsos of the user. The shoulder strap 27 can also be adjustable by trimming the strap at or around its distal end where fastener tab 24 is disposed in FIG. 1. In this regard, the user can adjust the length of the strap 27 to accommodate the desired compression to be applied to the user at the limb (e.g. the torso). Strap 27 can be operable to wrap over the shoulder of the user to hold the garment 10 in position.

Strap 27 as shown can extend away from the upper edge 21 of the body 20 and can include one or more compression portions. The one or more compression portions can be non-elastic and/or upraised portion(s) selectively positioned anywhere on strap 27 (e.g. at or around the proximal end, distal end, or any position therebetween) and operable to apply pressure to an area of the user. In this regard, the area of the user could be on or around the shoulder of the user. One or more compression portions can also be detachably connected to the strap 27. For example, if the fluctuation range is desirous of being adjusted, one or more compression portions of non-clastic material can be positioned on the outer surface of strap 27 after strap 27 after garment 10 has been donned by the user. In turn, an elasticity profile of the garment 10 can be adjusted from a first elasticity profile to a second elasticity profile. As a result, the range of compression fluctuation the garment 10 applies to the limb during normal wear changes.

A distal end of strap 27 may include a fastener tab 24 that is releasably attached onto the body 20 and/or spine portion 30. For example, when passing strap 27 over the shoulder of the user, the distal end with fastener tab 24 can be moved between one or more positions on the body 20 or spine portion 30 to adjust the tension in strap 27. When strap 27 is extendible about a shoulder of the user, it can be extended in the manner and shape similar to a t-shirt. Strap 27 can extend substantially orthogonal to edge 21 of body 20, substantially parallel to edge 29, or bands 32.

Figure 4:
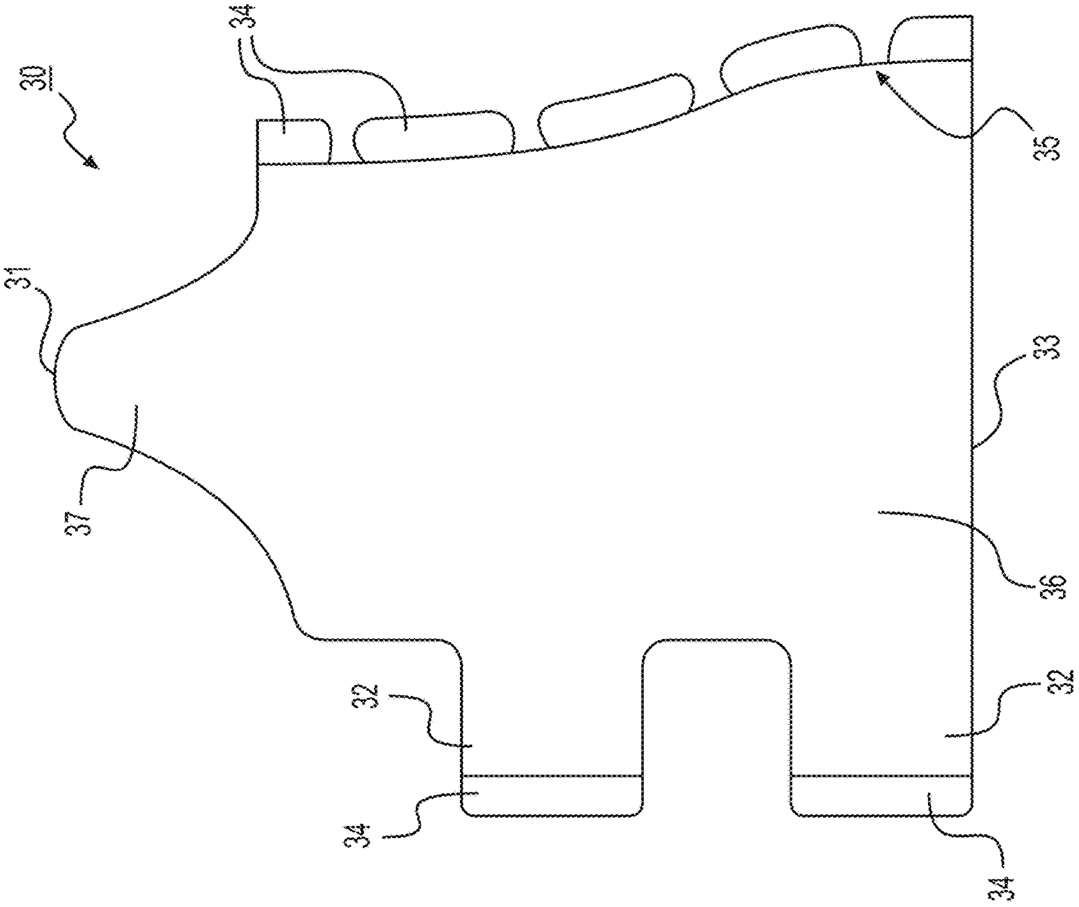
FIG. 4 depicts a close-up top plan view of an example spine portion for use with a compression garment of this disclosure.

One or more spine portions 30 as shown can be included and capable of being attached onto the body 20 to a plurality of different positions and/or independently angled to different orientations. As more clearly shown in FIG. 4, portion 30 can include a central region 36 as well as an upper edge 31 and a lower edge 33. As shown, edge 31 can be contoured and include one or more curved portions or regions 37. As previously described, portion 30 may have a plurality of tension bands 32 extending from an edge opposite body 20. Bands 32 can be of a stiffer material than the remainder of spine portion 30 and/or body 20. The body 20 can also be more clastic than bands 32 and/or spine portion 30 or of otherwise flexible, stretchable material. The flexible material can be capable of folding and conforming to contours of the torso thereby rendering the garment 10 less constricting. One or more of bands 32 can also be trimmable to adjust or conform to the torso, including its size and shape, of the user. Bands 32 can also include indicia for trimming. For example, the fastener tab 34 can initially be placed on a distal end of the band 32, a measurement can be taken about the user, the tab 34 can be removed, and the user can trim the band 32 to the desired dimension. After trimming, the fastener tab 34 can be repositioned on the band 32 and the distal end of band 32 can be moved to the desired location and orientation for the desired tension.

The body 20 can include an inner surface and an outer surface, the outer surface being stiffer or less flexible or less elastic than the inner surface. Bands 32 extending from one spine portions 30 can be wrapped partially around the patient and then be juxtaposed between the bands 32 of the other the spine portion 30 (or the opposite body 20 if bands instead extend from body 20 in those embodiments with only one spine portion 30). Bands 32 can be fastened onto the other of the spine portions 30 and/or the body 20. Bands 32 can include one or more detachable fasteners 34 (e.g. hook and loop fasteners such as Velcro®). The surfaces of body 20 and/or spine portion 30 can be covered with corresponding hook and loop surfaces. In some embodiments, bands 32 may extend past the corresponding opposite edge of body 20 and/or spine portion 30 (if applicable) and back onto their own portions respectively.

Spine portion 30 can be releasably attached onto body 20 in one of a plurality of different positions and/or orientations to accommodate the patient's limb as it may change shape or size over the course of treatment. It also renders the garment 10 capable of being used with any sized limb for multiple patients. As shown, the spine portion 30 can include one or more fastener tabs 34 disposed along an edge 35 that is opposite bands 32. The edge 35 can be contoured as a substantially flat, curved, a plurality curves, or some combination thereof. The fastener tabs 34 shown in FIGS. 1, 2 and 4 on edge 35 can be releasably attached thereon or permanently attached. There can be a space between each of the fastener tabs 34 or one or more can also be touching. In those embodiments with spacing, spacing between fastener tabs 34 can be selected so that garment 10 can conform to any three dimensional shape of the corresponding torso.

As previously discussed, body 20 can include indicia. In certain embodiments, edge 35 of spine portion 30 can be aligned with the indicia of body 20. For example, upper edge 31 of spine portion 30 can be aligned with the indicia on in one region of portion 20. Lower edge 33 of spine portion 30 can also be aligned with the indicia on the bottom 23 of body 20 corresponding to a dimension taken at about the lower edge of the torso.

Figure 2:
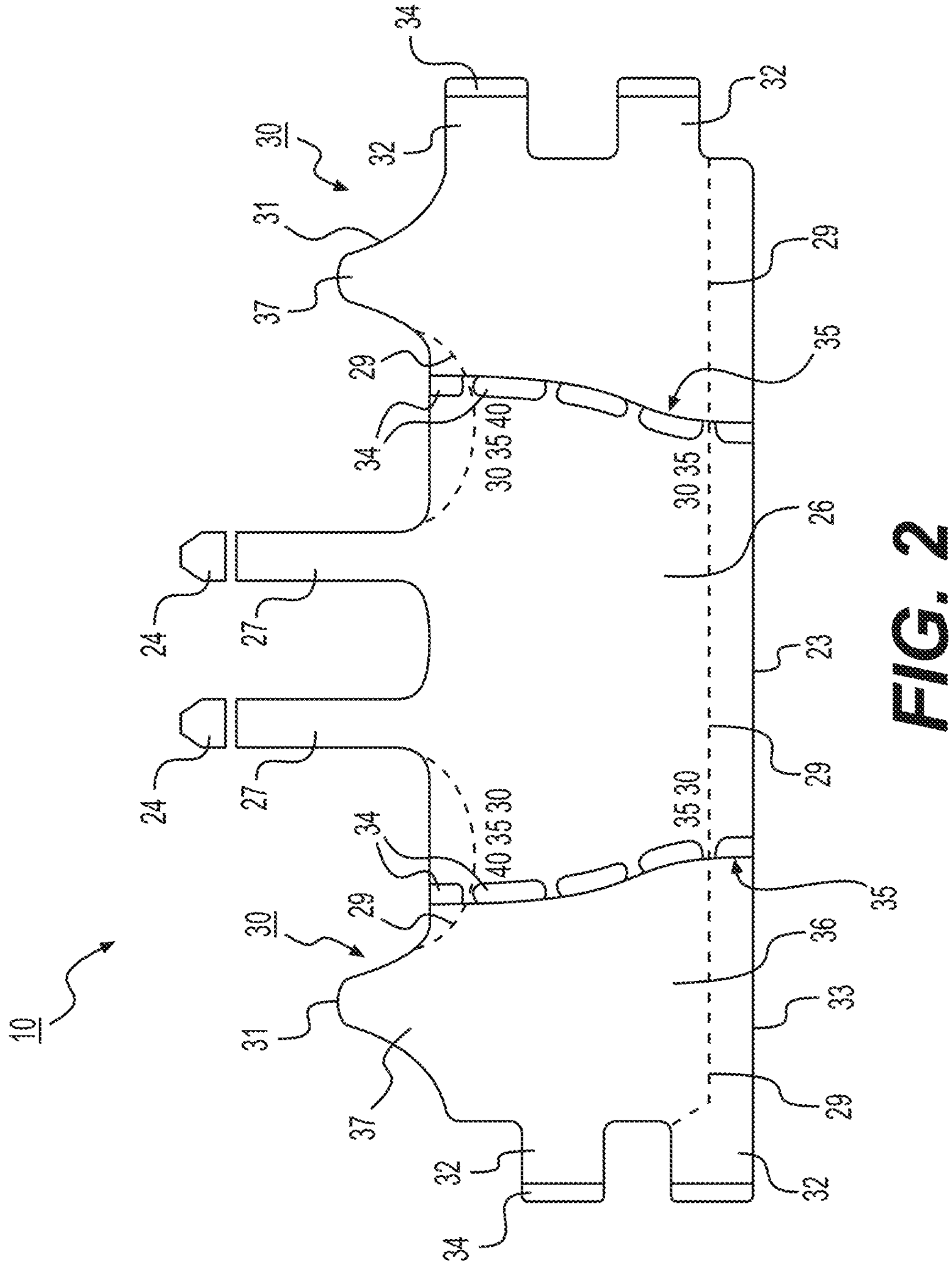
FIG. 2 depicts a top plan view of the garment of FIG. 1 in an assembled state.

Turning to FIG. 2, a top plan view of the garment 10 in an assembled state is depicted. As shown, body 20 can also include indicia 29 for indicating the axilla (e.g. the upper curved dashed lines in communication with each strap 27 of FIG. 2). The body 20, one or more of the tension bands 32, and/or one or more of straps 27 can include indicia indicating a dimension of the user, including a dimension of the shoulder, circumference of the upper chest, the lower chest, the torso, and/or the pectorals. One or more other indicia 29 can also be provided for trimming or adjusting garment 10 at other locations of the garment 10 (e.g. the indicia 29 disposed above the lower edges 23, 33 spanning across portions 20, 30.

Figure 5:
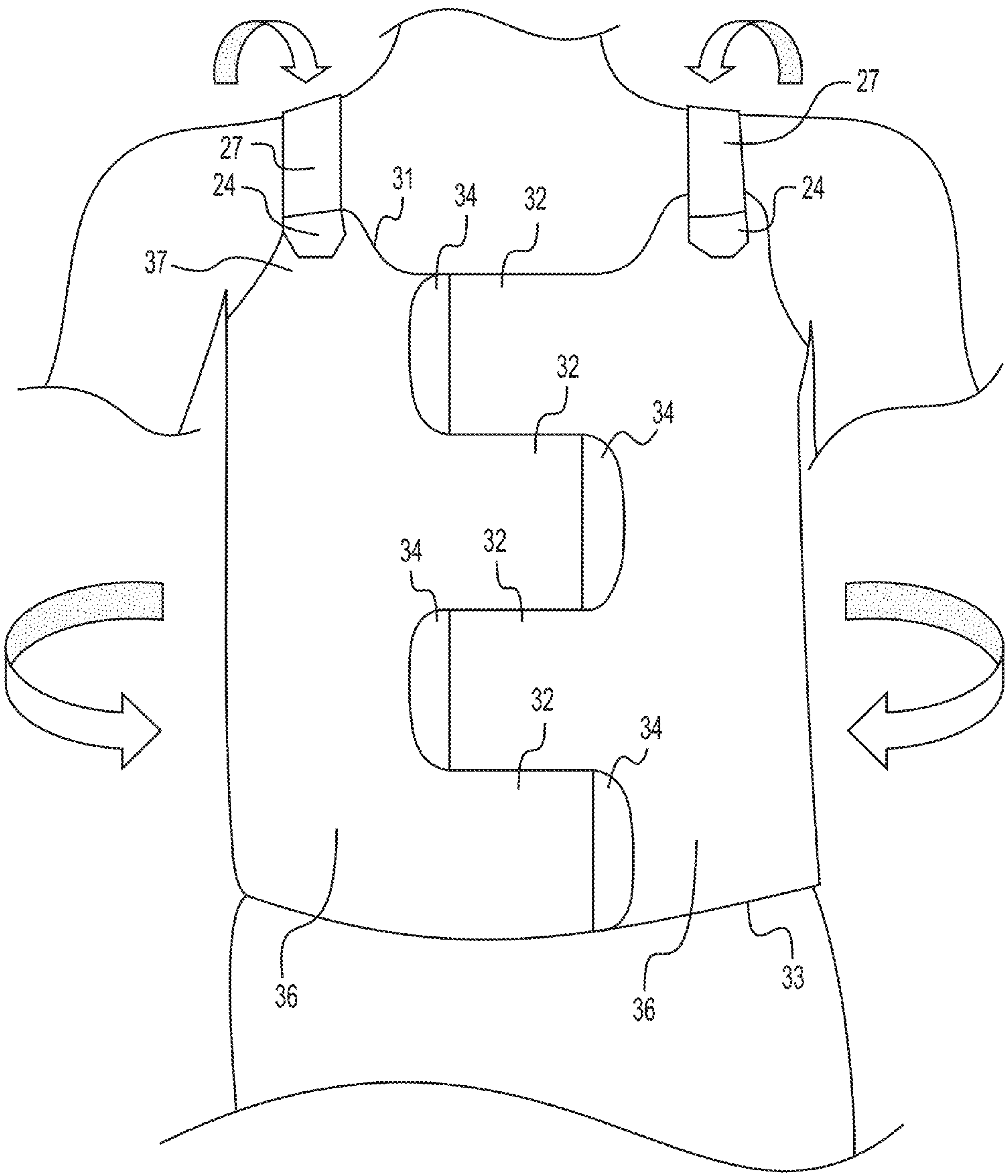
FIG. 5 depicts a perspective view of an example garment of this disclosure during fitting and/or attachment to a patient.

FIG. 5 depicts a perspective view of garment 10 of this disclosure during fitting and/or attachment to a patient. Garment 10 as shown has two lateral spine portions 30 that are wrapped around the torso and secured shut using each of bands 32 and straps 27. However, garment 10 is not so limited and instead of two lateral spine portions 30, only one spine portion 30 could be provided, more than two spine portions 30, or no spine portions 30 at all. As can be seen in FIG. 5, there are two straps 27 whose distal ends and corresponding fastener 24 have been brought over the respective shoulder of the user. Prior to or after being brought over and fastened on region 37 of body 20 (as depicted), one or both straps 27 can be trimmed to the appropriate dimension (e.g. length, width, etc.) and then re-positioned onto body 20 or spine 30. Region 37 can also include indicia so to facilitate adjustment of tension in strap 27 according to related compression or desired tightness. Each of bands 32 can also be wrapped around the torso of the patient as depicted and can be juxtaposed to increase or decrease the level of compression needed or desired. For example, fastener tab 34 of band 32 can be moved between one of a plurality of different positions and/or orientations and/or guided by corresponding indicia to selectively adjust the secured position of tab 34 on body 20 or spine portion 30. It is understood that the bands 32 may not necessarily be juxtaposed and instead bands 32 could overlap, could utilize D-rings to preclude juxtaposing, or the like.

Figure 6:
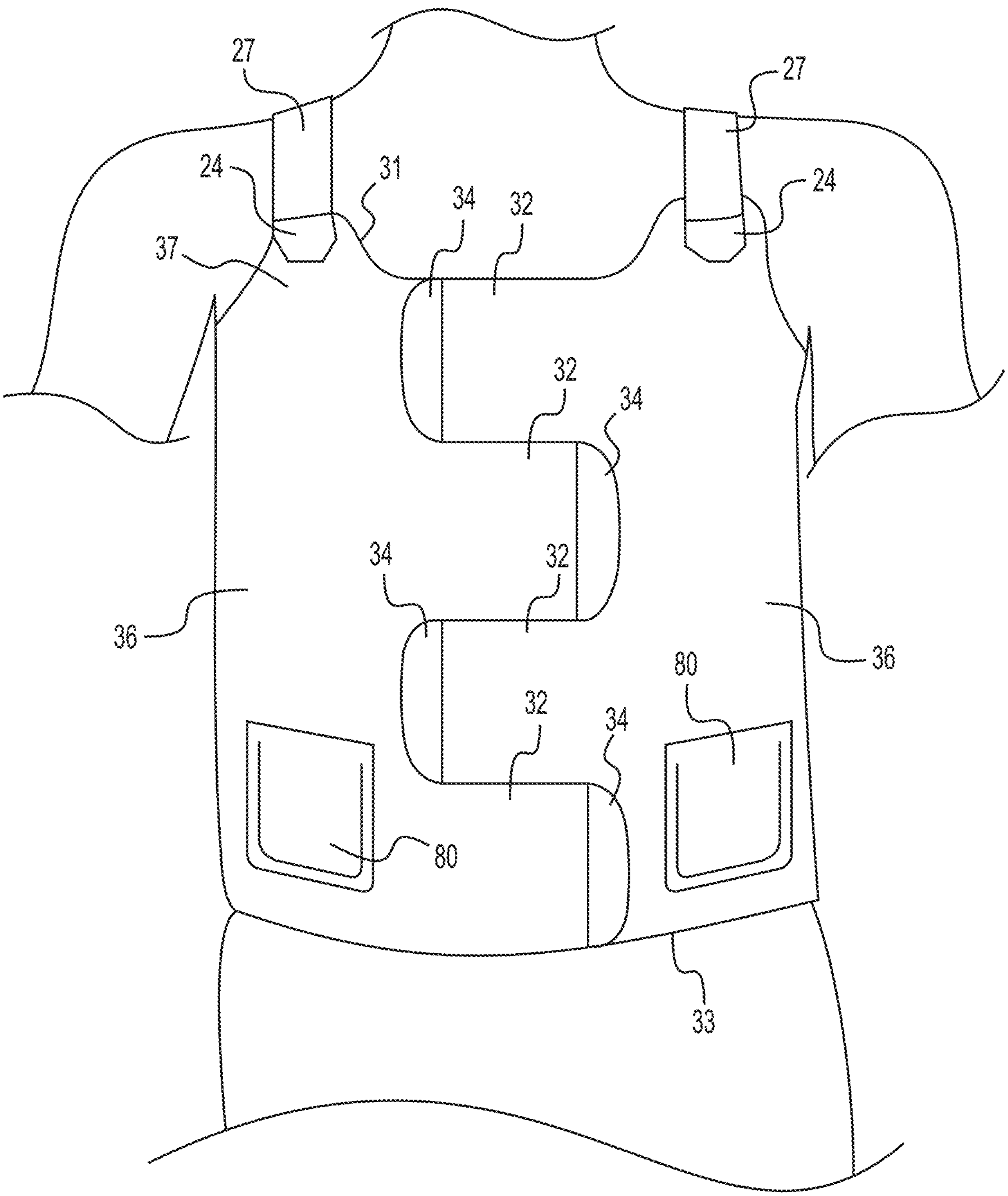
FIG. 6 depicts an example garment of this disclosure assembled and positioned on the user with adjustable pockets.
Figure 7:
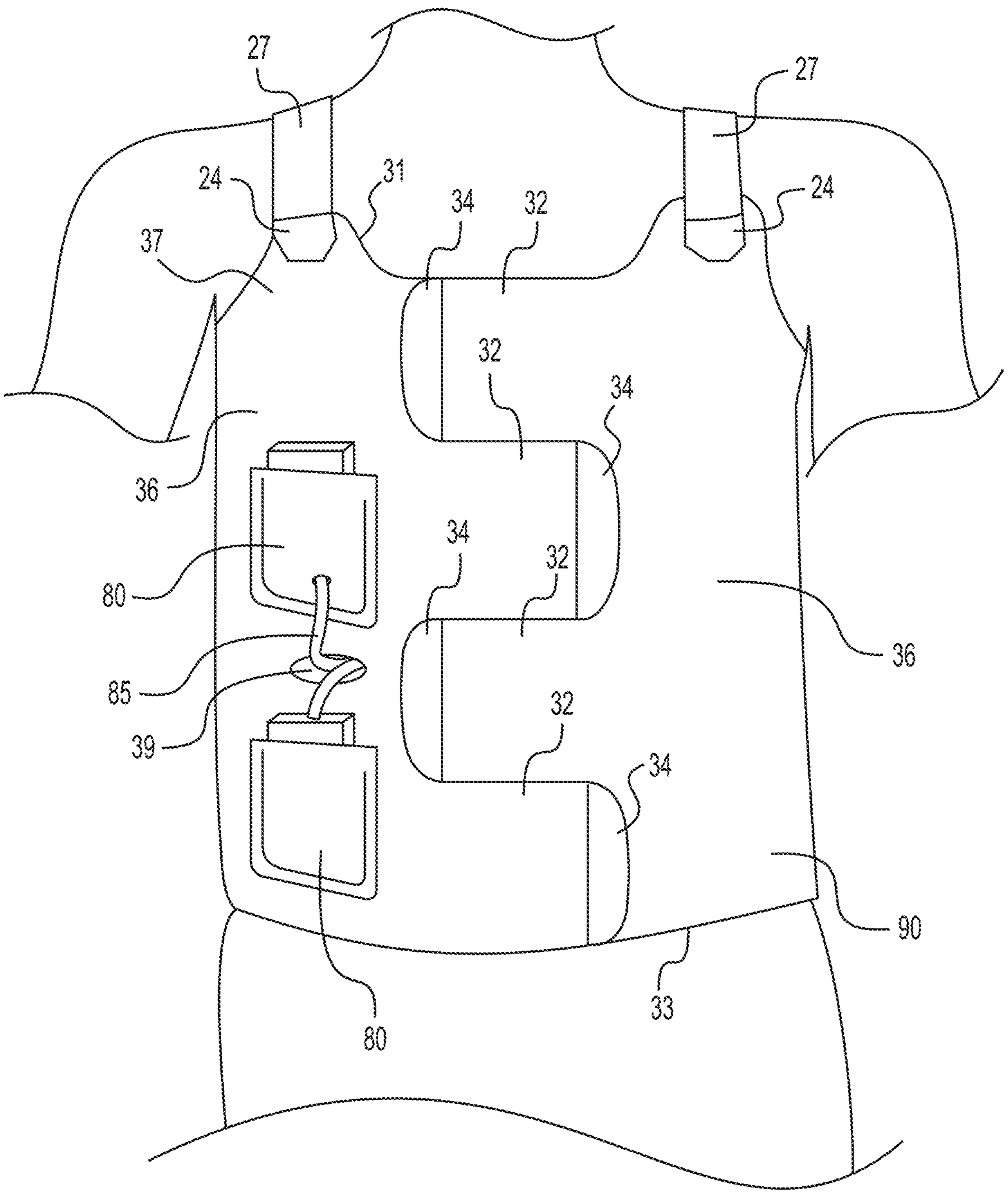
FIG. 7 depicts an example garment of this disclosure assembled and positioned on the user with adjustable pockets with one or more holes cut therein order to accommodate wire leads.

FIG. 6 depicts an embodiment of garment 10 also assembled and positioned on the user with adjustable pockets 80. As shown, portions of garment 10, including body 20 or spine portion 30, can also include one or more pockets 80. The pockets 80 can be of any shape, material, and be capable of securely receiving one or more devices or articles for use by the patient. Pockets 80 can be permanently positioned or releasably attached in any number of positions and/or orientations on garment 10. For example, FIG. 7 depicts an example garment 10 with adjustable pockets 80 in a different location and similar orientation than in FIG. 6 with one or more holes 39 cut or positioned in garment 10 to accommodate wire leads. This is particularly advantageous for those patients who, for example, may use a sensor operatively connected to a heart monitor being held in a pocket. In the depicted example, the patient needs to be able to lay on their left side such that any monitors in communications with pockets 80 and corresponding leads 85 need to be on the opposite, right side. The capability of selectively and customizing size and/or location of holes 39 allows the patient and/or therapist to trim the garment 10 in order to freely position the pockets 80 and wire leads 85 wherever it is most suitable. However, if the user would prefer not cut the garment 10, then the wires 85 could easily be passed in between the juxtaposed bands 32, or the fastener tabs 34.

Figure 8:
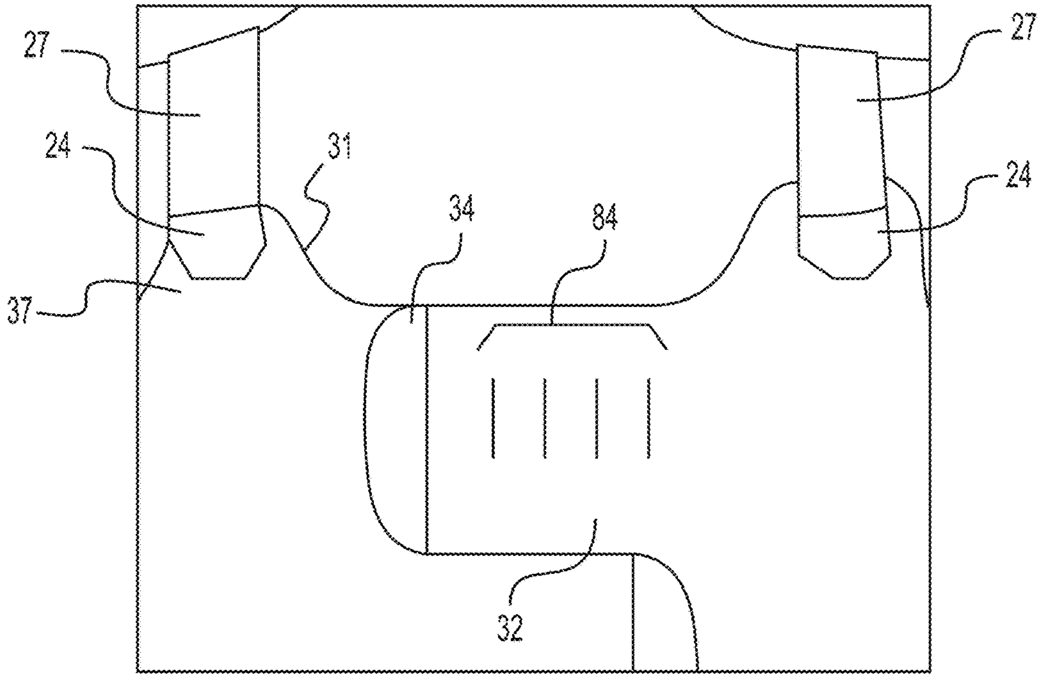
FIG. 8 depicts an embodiment of the garment with an exemplary compression measuring system that includes indicia on an exemplary band.
Figure 8:
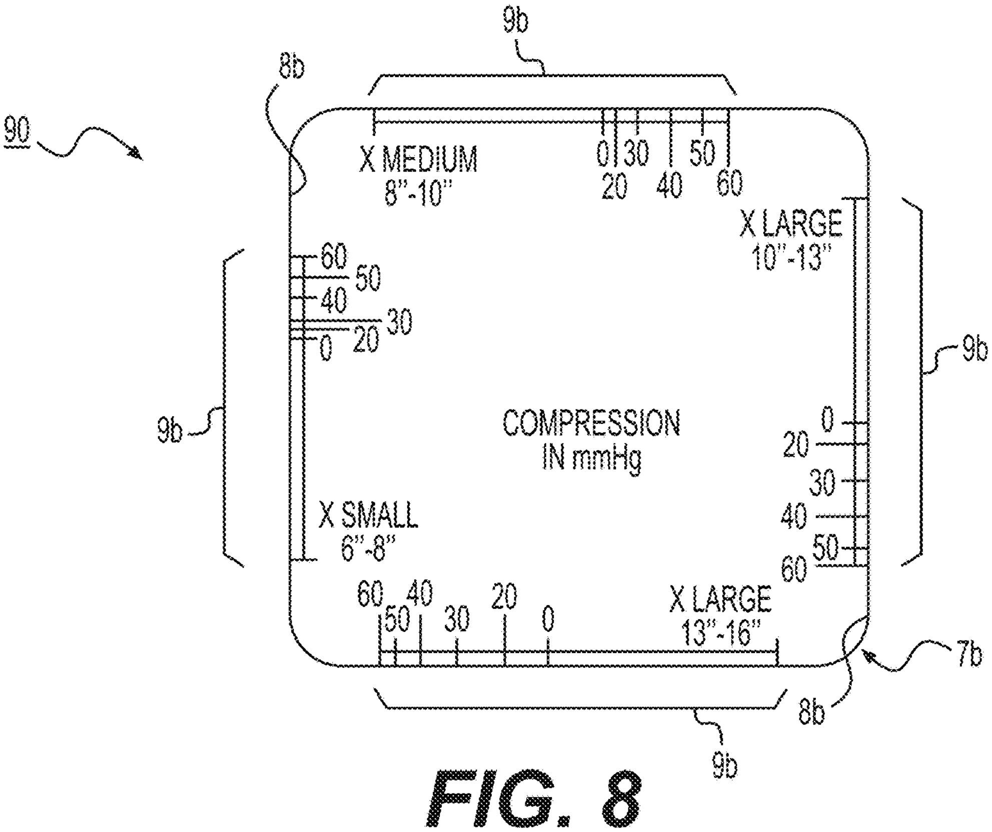

FIG. 8 shows an exemplary compression garment 10 including bands 32 with an exemplary compression measuring system. Each band 32 may be elastic or substantially elastic along its length or longitudinal axis (e.g. the axis along which tension is to be applied). Each band 32 may alternatively be elastic along only a part of its length. Each band 32 may have visual indicators such as indicia 84 printed along its elastic length, or elastic axis, spaced by intervals. Each interval may have a fixed or specified length when respective band 32 is not under tension. Each of bands 32 may be pulled under tension around the torso at a selected location, attached to itself and/or attachable to other portions of garment 10, using a fastener 34 and thus applying compression to that portion of the torso.

As can be seen, indicia 84 may include one or more tick marks spaced along band 32 at intervals. However, indicia 84 is not so limited and could include dots, geometric shapes, symbols, patterns, text, or the like spaced at intervals therealong for measurement with the referenced measuring device such as a calibrated scale or card upon donning of each band 32. Each interval may be spaced at a predetermined distance from each other when the bands 32 are unstretched. In contrast, when a band 32 is under tension, the spacing between each indicia 84 may serve to accurately measure compression delivered by garment 10 to the torso at one or more multiple locations. For example, an interval between successive indicia 84 may increase when band 32 is under tension and lengthens. The distance between successive indicia 84 may then be measured after application of garment 10 to the torso, wherein the measured distance may indicate tension in band 32 and in turn the specific amount of compression applied by garment 10 to the torso.

Figure 9A:
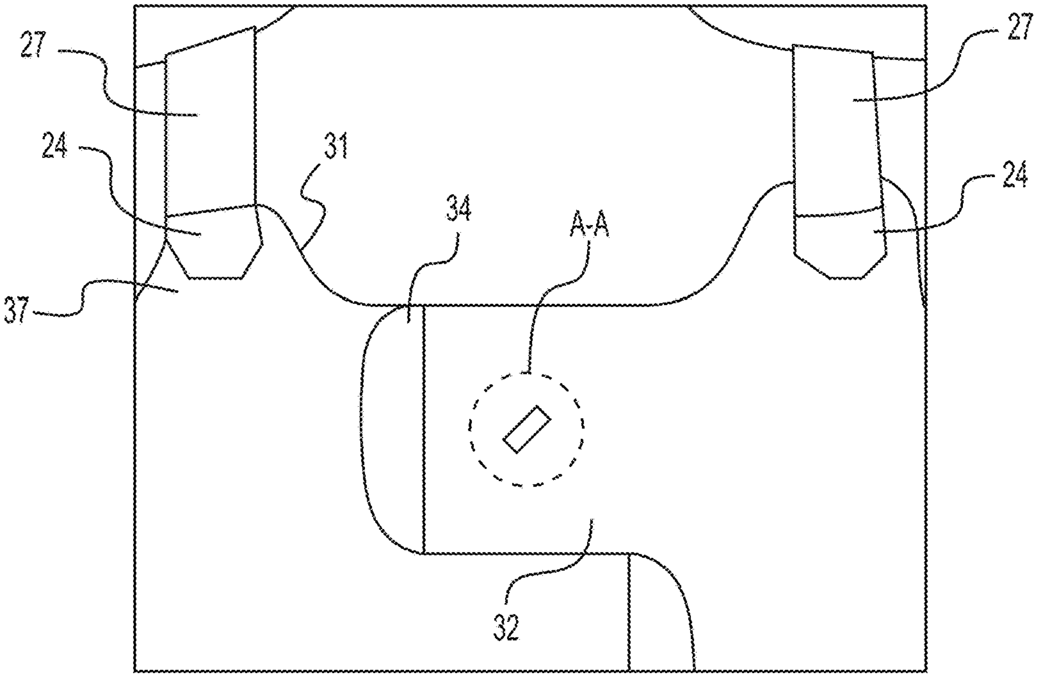
FIG. 9A depicts a close up view of an example band of the garment with an exemplary multi-layer compression measuring system.
Figure 9B:
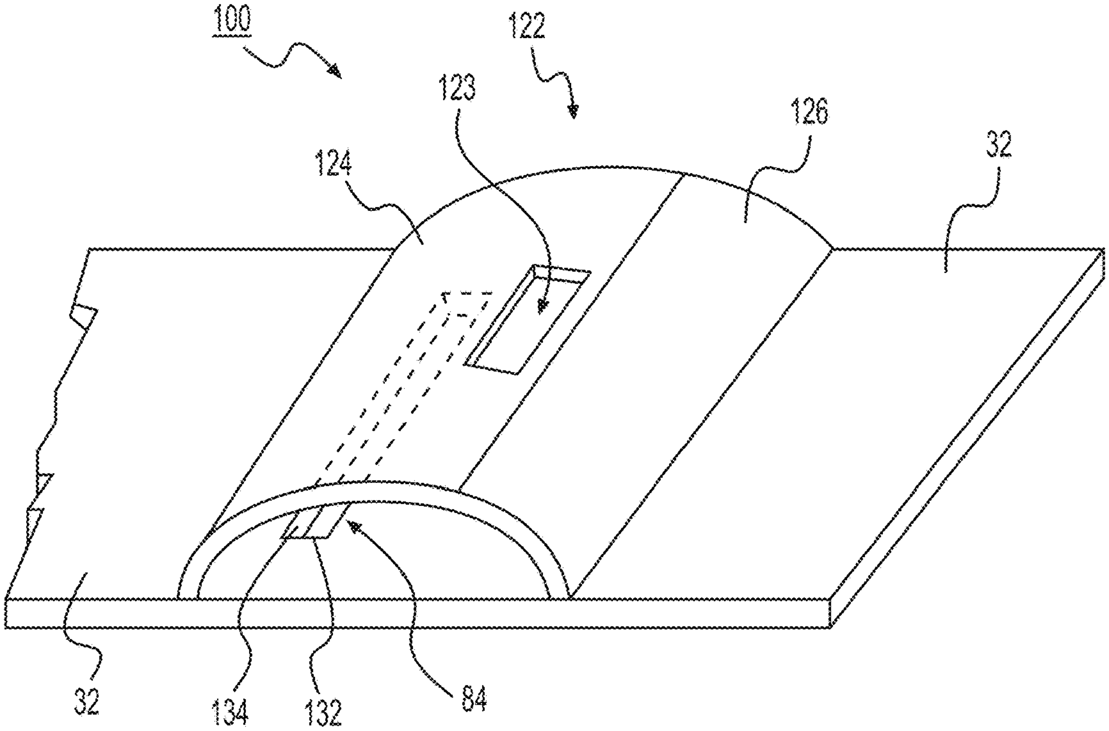
FIG. 9B depicts a close up view of plane A-A of FIG. 9A with an exemplary multi-layered compression measuring system in one of the bands prior to stretching.

Systems of measuring compression levels and/or tension associated with bands 32 and garment 10 are also contemplated such as using the card 90 shown in FIG. 8. Card 90 may be used to determine tension at multiple locations of band 32 as well as multiple locations about the torso when assembled with garment 10. After measuring, band 32 can optionally be removed, relocated, and/or adjusted by releasing fastener 34, selectively positioning said fastener 34, and re-fastening fastener 34 to the selected location, orientation, and/or desired tension. Card 90 may include reference numerals 7*a*-7*c* disposed adjacent a plurality of edges 8*a*-8*c* with measurement scales 9*a*-9*c* calibrated to measure the distance between indicia 84 in the bands 32. FIGS. 9A through 9B show certain non-limiting embodiments of a multi-layer compression measurement system 100 for use with one or more of bands 32 and/or any portion of body 20.

Figure 10A:
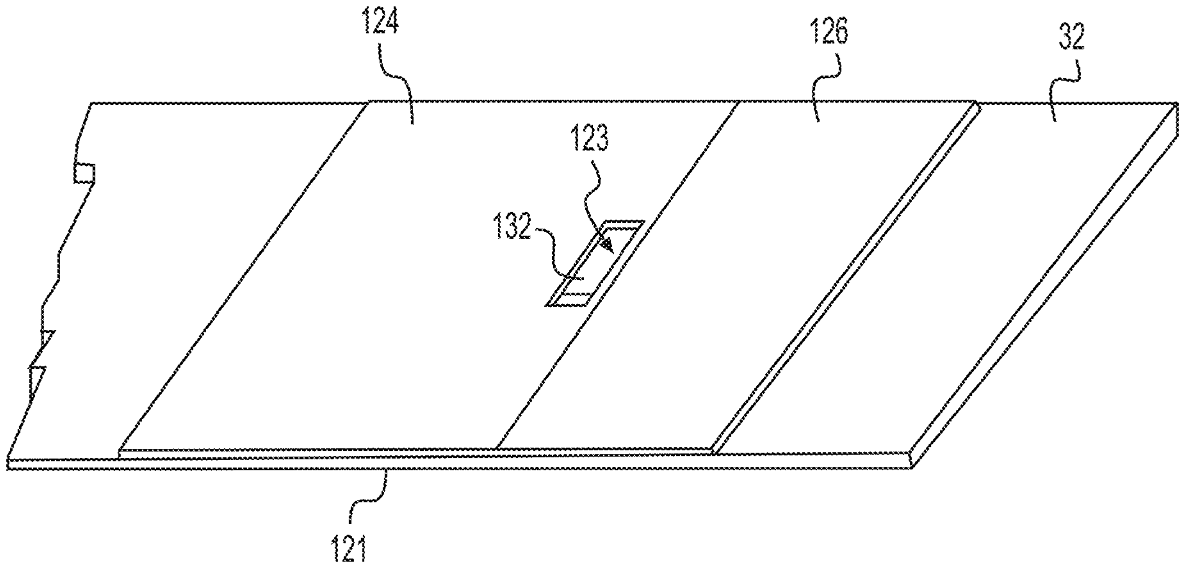
FIG. 10A is a perspective view of the measurement system of FIG. 9B with a predetermined tension applied to the band.
Figure 10B:
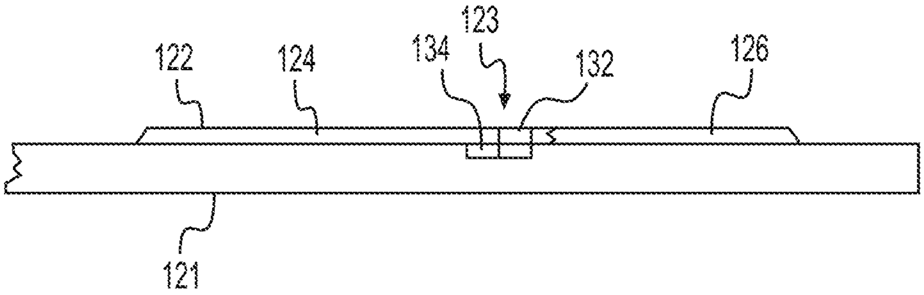
FIG. 10B is a sectional side elevation view corresponding to FIG. 10A.

System 100 can be installed in one or more bands 32 of the garment 10 as shown in FIGS. 9A through 9B but can be incorporated in any portion of garment 10 including portions of portion 20. FIG. 9B is a perspective view of system 100 including a stretchable base layer 121 having indicia 84 thereon; and a stretchable upper layer 122 positioned on top of the stretchable base layer. Importantly, stretchable upper layer 122 comprises a first portion 124 and a second portion 126 joined end-to-end. Importantly as well, first portion 124 and second portion 126 can have different stiffnesses. For example, first portion 124 may be inelastic and second portion 126 may be elastic. One end of first portion 124 is attached (e.g.: sewn) to base layer 121 and one end of second portion 126 is also attached (e.g.: sewn) to base layer 121, as illustrated. The other ends of first and second portions 124 and 126 are also attached (e.g.: sewn) together, as also illustrated. FIG. 10A is a perspective view of the measurement system 100 of FIG. 9B with a predetermined tension applied to the band 32. FIG. 10B is a sectional side elevation view corresponding to FIG. 10A.

It is to be understood that either or both of the two layers in system 100 may in turn be made of two, three or more layers or sections connected together, and therefore any references in the specification and claims to two layers refer to at least two layers, each made of one, two, three or more layers or sections connected together. Additionally, indicia 84 may be positioned on system 100 by being printed, painted, glued, heat transferred, sewn onto or otherwise attached to the upper surface of base layer 121. In one preferred embodiment, indicia 84 comprise marking 132 and a red marking 134. In other embodiments, the indicia may comprise a tension force scale calibrated to display different tension levels. In operation, indicia 84 can be seen by a user through window 123 in first portion 124 of top layer 122. Other potential systems of measuring can include tension strain gauges, pressure sensors, and/or other bio-feedback sensors in one or more locations of the garment.

Figure 11:
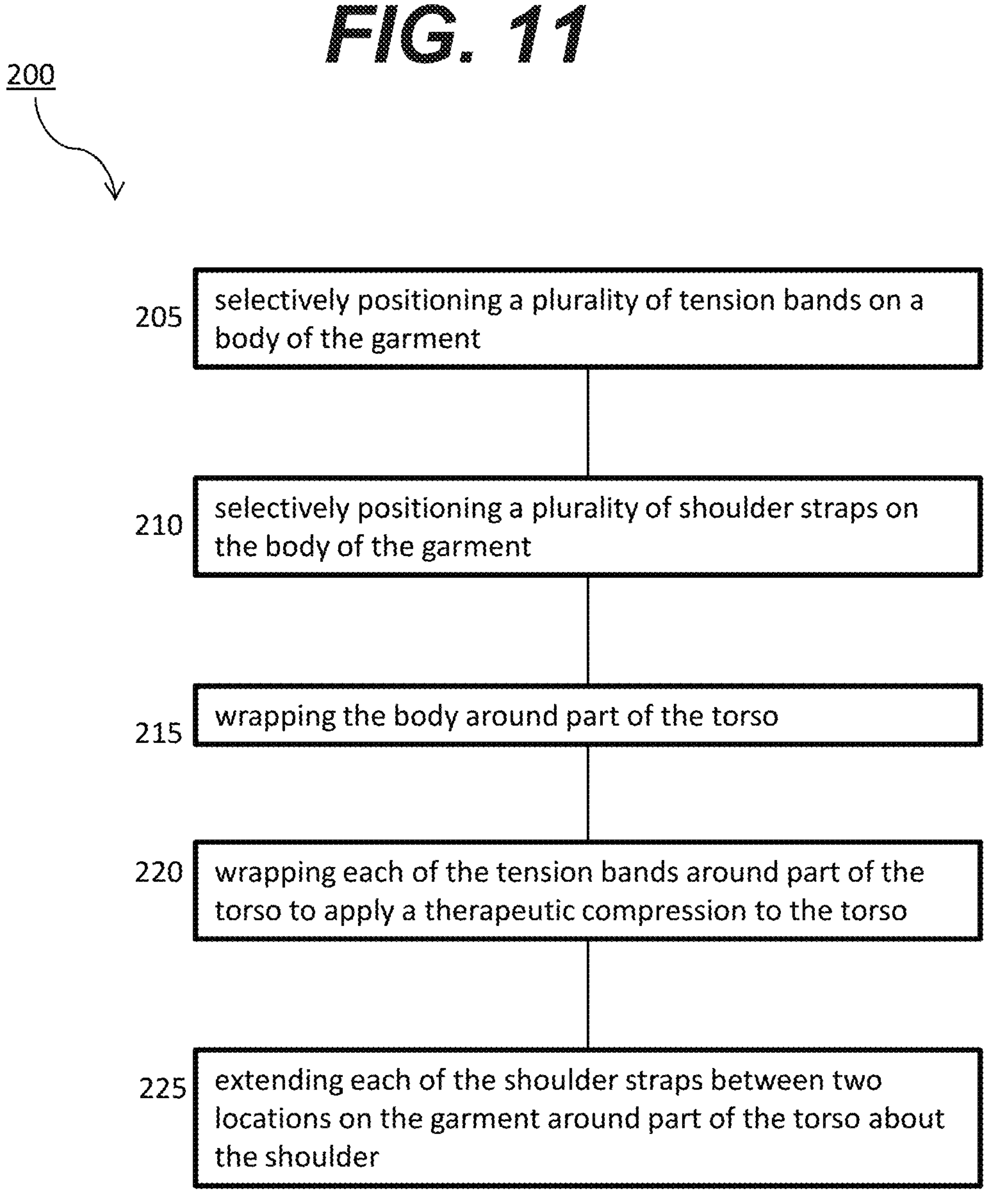
FIG. 11 depicts a schematic overview of a method of assembling an example garment of this disclosure.

FIG. 11 depicts a schematic overview of a method 200 of assembling an example garment of this disclosure. The method can include 205 selectively positioning a plurality of tension bands on a body of the garment; 210 selectively positioning a plurality of shoulder straps on the body of the garment; 215 wrapping the body around part of the torso; 220 wrapping each of the tension bands around part of the torso to apply a therapeutic compression to the torso; and 225 extending each of the shoulder straps between two locations on the garment around part of the torso about the shoulder.

Unlike other solutions, the herein disclosed compression garment is capable of being customized at the point of application so that it will fit almost any individual. The main body and/or spine portion(s) of the compression garment can be made from inelastic laminate materials, clastic materials, and/or can be tailored by both length and width in order to conform to the user's torso regardless of shape, gender and anatomy. The axilla region of the compression garment can be trimmed and adjusted to minimize potential irritation. The shoulder straps can be tailored to maximize fit and function. The laminate material of the compression garment also can allow the garment to be cut in almost any location without the risk of the material unraveling or compromising the integrity of the garment. The band closure system provides further adjustability to fit male and female anatomies and edematous contours.

Other solutions are typically constructed of materials incapable of being trimmed which prevent the level of customization offered by the herein disclosed compression garment. A plurality of adjustable bands of the garment may be included that allow the user to tailor the level of compression and target specific locations as needed. Prior solutions typically offer nonadjustable compression with the level of compression limited to the elasticity and power of the materials being used.

Additionally, when being used for post-surgical support, the adjustable pockets in certain embodiments of the garment can be used for holding devices such as monitors and can be positioned wherever it makes the most sense for each individual patient. The laminate material that may be used with the garment can also allows one or more holes to be cut at almost any location in order to optimize positioning. Most postsurgical support garment include pockets and opening to run the lead wires, however they are in a fixed location and cannot be moved to accommodate individual needs.

Whereas as previous approaches have been primarily based on using thin elastic materials in an effort to keep costs down and maximize comfort, the herein disclosed compression garment resolves problems of the art through an inelastic trimmable material that can be customized to the truncal region for each and offer a completely new approach when applying compression.

The herein disclosed compression garment effectively contours the intricate shape of the human torso effectively enough to provide therapeutic compression. The herein disclosed garment overcomes those problems that have plagued the art, including trimming away an area(s) of excess material, adjustability of dimensions and compression, and comfort. In order for the garment to function as a form of compression therapy, the trimmed section can permit the garment to more effectively contour the shape of the torso. The disclosed garment does just that by enabling the user or therapist to customize features of the garment in accordance with the torso of the patient to optimize the fit, healing following surgery, and/or therapeutic compression.

Further, the inelastic material(s) and adjustable band(s) allow the user/therapist to specifically tailor the level of compression to maximize treatment such that unlike the current elastic options that are available, the inelastic properties offer that added benefit of providing more compression in times of stress. For example, when being used for post-surgical support, when the chest cavity expands putting strain on the incision site, the inelastic properties cause the compression level to increase offering additional support. When being used to treat edema, the adjustable bands and sizing also allow the user to maintain the desired compression level even after they have reduced, and if the reduction is significant enough they can resize the garment and/or bands instead of having to obtain a smaller size before treatment can continue.

This solution will permit end-users, including medical professionals and therapists, to have one garment on a torso that can fit any patient without having to measure the chest, waste, or other relevant dimensions of the patient to determine product size. This enables end-users to start treatment immediately, similar to bandaging. However, unlike bandaging, zipper garments, or bra-like products, the herein disclosed garments simplify self-management, which allows the patient to adjust the garment as swelling reduction is achieved or treatment progresses thus improving results.

The herein disclosed garment also allows the patient to easily remove and reapply their garment which promotes better hygiene.

If a stiffer, short stretch material (e.g. non-elastic material) can be used for the entire garment, it can be to constricting and uncomfortable. If a more elastic material is used, the band closures on the front of the garment tend to cut and fold into soft areas of the body such as the chest and abdomen. The solution garment of this disclosure may function best when the forward bands are constructed of a stiffer material, while the rear portion (e.g. body and/or portions of the spine portion) of the garment, that is trimmed to size, is made from a more elastic material. The stiffer material in the front of the garment can bridge the folds and body contours properly while the back material can make it less constricting and more comfortable.

Other features and advantages of the compression garment will be apparent from the description herein. The examples are provided herein are solely to illustrate the garment by reference to specific embodiments. These exemplifications, while illustrating certain specific aspects of the garment, do not portray the limitations or circumscribe the scope of the disclosed invention. Many variations to those described above are possible.

What is claimed is:

1. A compression garment, comprising:

a body dimensioned to wrap at least partially around the back of a torso of a user, a plurality of spine portions dimensioned to wrap at least partially around the front of a torso of a user, wherein at least one edge or region indicia of each spine portion is trimmable, each spine portion being releasably positionable onto the body at a plurality of positions;

a plurality of tension bands positioned along each of the plurality of spine portions, and at least one adjustable shoulder strap extended from at least one of the plurality of spine portions, wherein the at least one adjustable shoulder strap is operable to wrap over a shoulder of the user between two positions of the garment to hold the garment in position, wherein the at least one adjustable shoulder strap comprises at least one compression portion, the at least one compression portion is inelastic, and wherein the plurality of spine portions are inelastic and the body is elastic.

2. The garment according to claim 1, wherein the plurality of spine portions consists of two spine portions, each spine portion being removably positioned on opposite side edges of the body.

3. The garment according to claim 1, wherein the body comprises indicia indicating a dimension of the user to trim the body to conform to the torso of the user.

4. The garment according to claim 1, wherein trimming the body along the indicia does not change the length of the body.

5. The garment according to claim 1, wherein the tension bands are substantially elastic.

6. The garment of claim 1, further comprising a compression and/or tension level measuring system in the garment for indicating an actual compression level delivered to the torso by the garment.

7. The garment according to claim 6, wherein the measuring system is disposed in the body, the at least one shoulder strap, at least one spine portion of the plurality of spine portions, or one or more of the tension bands.

8. A method of fitting a compression garment to a torso, comprising:

selectively positioning a plurality of tension bands on a body of the garment;

selectively positioning a plurality of shoulder straps on the body of the garment;

wrapping the body around part of the torso;

using indicia to trim the spine portion to fit with the torso;

wrapping each of the tension bands around part of the torso to apply a therapeutic compression to the torso; and extending each of the shoulder straps between two locations on the garment around part of the torso about a shoulder.

9. A compression garment, comprising:

a body dimensioned to wrap at least partially around the back of a torso of a user, a plurality of spine portions dimensioned to wrap at least partially around the front of the torso of the user, wherein at least one lateral side edge or region indicia of each spine portion is trimmable, each spine portion being releasably positionable onto the body at a plurality of positions;

a plurality of tension bands integrally formed with and extending from each of the plurality of the spine portions, wherein the plurality of tension bands on one of the plurality of spine portions are positioned and adapted to be releasably positioned in juxtapose arrangement relative to the plurality of tension bands on another of the plurality of spine portions, and at least one adjustable shoulder strap extended from at least one of the plurality of the spine portions, wherein the at least one adjustable shoulder strap is operable to wrap over the shoulder of the user between two positions of the garment and attach to the body to hold the garment in position, wherein the at least one adjustable shoulder strap comprises at least one compression portion, the at least one compression portion is inelastic, and wherein the plurality of spine portions are inelastic and the body is elastic.

10. The garment according to claim 9, wherein the plurality of spine portions consists of two spine portions, each spine portion being removably positioned on opposite side edges of the body.

11. The garment according to claim 9, wherein the body comprises indicia indicating a dimension of the user to trim the body to conform to the torso of the user.

12. The garment according to claim 9, wherein trimming the body along the indicia does not change the length of the body.

13. The garment according to claim 9, wherein the tension bands are substantially elastic.

14. The garment according to claim 9, further comprising a compression and/or tension level measuring system in the garment for indicating an actual compression level delivered to the torso by the garment.

15. The garment according to claim 14, the compression and/or tension level measuring system being disposed in the body, the at least one shoulder strap, at least one spine portion, or one or more of the tension bands.

* * * * *